United States Patent [19]

Matsubayashi

[11] Patent Number: 4,649,555
[45] Date of Patent: Mar. 10, 1987

[54] X-RAY COMPUTERIZED TOMOGRAPHIC APPARATUS

[75] Inventor: Takayuki Matsubayashi, Tochigi, Japan

[73] Assignee: Tokyo Shibaura Denki Kabushiki Kaisha, Kawasaki, Japan

[21] Appl. No.: 445,751

[22] Filed: Nov. 30, 1982

[30] Foreign Application Priority Data

Dec. 1, 1981 [JP] Japan .................................. 56-191798

[51] Int. Cl.$^4$ .......................... G01N 23/00; A61B 6/08
[52] U.S. Cl. .......................................... 378/4; 378/20; 378/99; 378/205
[58] Field of Search ...................... 378/4, 901, 20, 165, 378/205, 91, 98–100

[56] References Cited

U.S. PATENT DOCUMENTS

| 3,936,712 | 2/1976  | Gerber .................................. 318/628 |
| 4,032,784 | 6/1977  | Rich ..................................... 378/108 |
| 4,135,247 | 1/1979  | Gordon et al. ...................... 378/901 |
| 4,174,481 | 11/1979 | Liebetruth .......................... 378/20  |
| 4,245,244 | 1/1981  | Lijewski ............................. 378/99  |
| 4,259,721 | 3/1981  | Kuznia ............................... 378/901 |
| 4,259,725 | 3/1981  | Andrews ............................ 378/901 |

FOREIGN PATENT DOCUMENTS

| 0004258 | 10/1979 | European Pat. Off. ................ 378/4 |
| 2655661 | 6/1978  | Fed. Rep. of Germany .......... 378/4 |
| 2705640 | 8/1978  | Fed. Rep. of Germany .......... 378/4 |

OTHER PUBLICATIONS

Sales information from a poster exhibit presented by G.E. at RSNA, 1980.
Farmer et al, "Cine CT Captures the Beating Heart", Diagnostic Imaging, Oct. 1984.

Primary Examiner—Craig E. Church
Assistant Examiner—Charles F. Wieland
Attorney, Agent, or Firm—Cushman, Darby & Cushman

[57] ABSTRACT

In an X-ray computerized tomographic apparatus for utilizing a Scanographic scanning operation prior to a CT scanning operation, it is desirable to designate a plurality of CT scanning portions of the patient by using a horizontal line on a display screen where intervals between successive lines are freely adjustable in accordance with the portions of the patient's body which will receive the CT scanning. To this end, there is provided a converting means for converting the X-ray data from a detector array into actual position data for the patient who will be scanned in the CT mode.

2 Claims, 4 Drawing Figures

X-RAY COMPUTERIZED TOMOGRAPHIC APPARATUS

BACKGROUND OF THE INVENTION

This invention relates generally to a computerized tomographic apparatus; relates more specifically to an X-ray computerized tomographic apparatus utilizing a Scanography operation prior to the CT scanning operation.

Within recent years it became well known in the medical diagnostic field to employ an X-ray type computerized tomographic apparatus utilizing so-called "SCANO graphic image" taken prior to the normal "computerized tomographic image".

In X-ray computerized tomographic apparatus (referred to "CT apparatus" hereinafter) of the third and subsequent generation types, i.e., "fan beam type" X-ray tomographic apparatus, a patient is subjected to the Scanographic scanning operation prior to the CT scanning operation, to specify or determine a tomographic scanning portion from the displayed X-ray image. For the Scanographic scanning operation, an X-ray tube and an X-ray detector array of the X-ray CT apparatus are arranged to the fixed (stationary) position, and a patient couch on which the patient is laid is translated along the longitudinal axis thereof between the X-ray tube and the X-ray detector. Under this condition, X-rays are irradiated toward the patient in synchronism with the movement of the patient couch. A Scanographic image thus obtained is equivalent to an ordinary X-ray penetration type two-dimensional image.

The CRT display unit of the X-ray CT apparatus displays on the screen simultaneously the Scanographic image and "horizontal lines" equidistantly arranged for indicating possible tomographic scanning portions. After seeing the Scanographic image, an operator specifies tomographic scanning portions and keys in given numbers which, for example, could be displayed in the vicinity of the left corner on the screen aligned in the vertical direction. After this key-in operation, the patient couch is translated to position the designated tomographic scanning portion directly under the X-ray tube. Then the X-ray CT apparatus begins scanning the patient in a rotary manner.

However, the conventional X-ray CT apparatus is restricted to designate CT scanning portions of the patient by way of a plurarity of the above-mentioned "horizontal lines" of which intervals between the succeeding horizontal lines are predetermined, i.e., cannot be adjustable. In particular, when a plurality of tomographic scanning portions are required to be scanned, these portions must be specified for every individual scanning operation. Thus, the scanning operation by the conventional apparatus is troublesome and time-consuming.

Accordingly, an object of the present invention is to provide an X-ray computerized tomographic apparatus which first can designate CT scanning portions on the Scanographic image with free-adjustable "horizontal lines", and secondly can automatically perform the positioning of the X-ray irradiation toward the object for CT scanning on specified portions of the Scanographic image in a predetermined order.

SUMMARY OF THE INVENTION

The X-ray computerized tomographic apparatus utilizing a Scanographic scanning operation prior to the CT scanning operation, according to the invention, comprises: source means for providing an X-ray irradiation penetrating through a object to be examined so as to produce image data representative of the density of the object in a cross-sectional plane; couch means on which the object is laid and which is slidable along a longitudinal axis of the object; detector means for receiving the X-ray irradiation penetrating through the object along a plurality of paths and for producing digital output signals representative of irradiation intensity received; scanning means for providing translation of the couch means during the Scanographic image scanning operation for providing relative rotation of the source and detector means with respect to the object during the computerized tomographic scanning operation, and for periodically causing emission of the X-ray irradiation from the source means during both the Scanographic image and the computerized tomographic scanning operations; display/diagnostic control means including a display section by which the Scanographic and the computerized tomographic images of the object are displayed, and a section for determining the computerized tomographic scanning position from the displayed Scanographic image by means of a movable and visual horizontal line on the display section; and central control means including a memory section for storing data signals relating to the computerized tomographic image of the object derived from the detector means and to the relative position of the X-ray irradiation source means with respect to the object on the couch means, and a processor section for processing the differences between the computerized tomographic image position and the corresponding X-ray irradiation source position to translate the object on the couch means along the longitudinal axis thereof until said differences becomes zero for the computerized tomographic scanning operation.

BRIEF DESCRIPTION OF THE DRAWINGS

The invention is best understood by reference to the accompanying drawings, of which.

DETAILED DESCRIPTION OF THE PREFERRED EMBODIMENT

Figure 1:
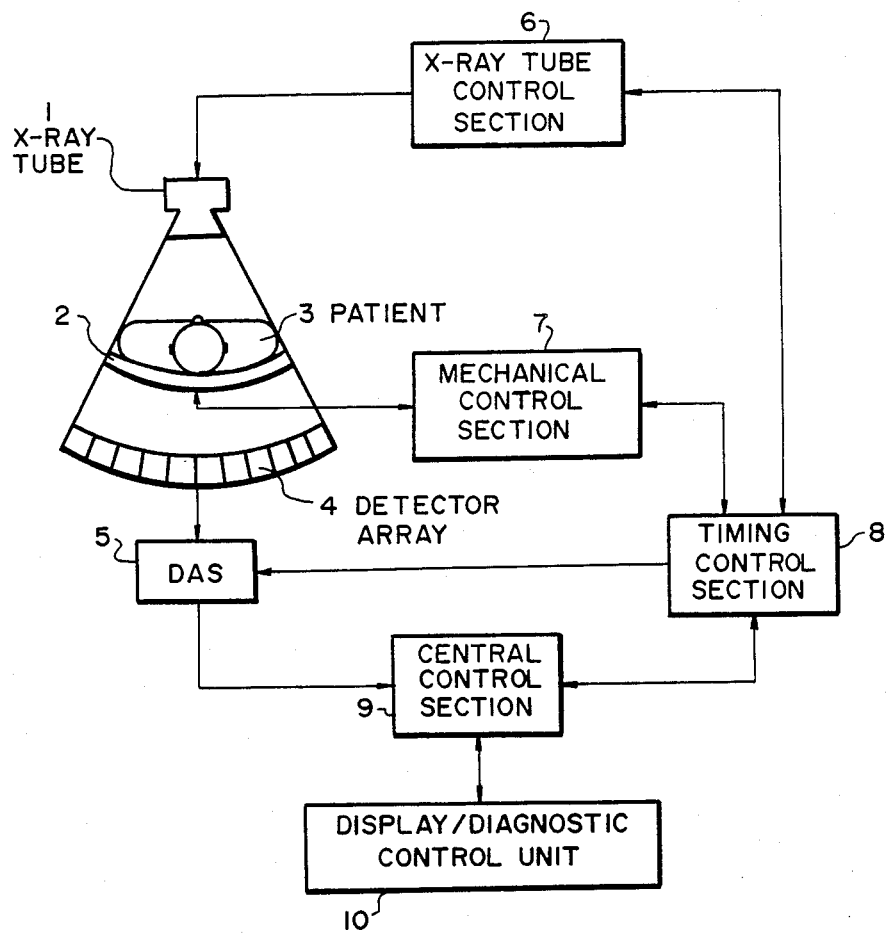
FIG. 1 shows schematically a block diagram of one embodiment according to the invention.

Referring to FIG. 1, there is shown a block diagram of an embodiment of an X-ray CT apparatus according to the present invention. In the figure, reference numeral 1 denotes an X-ray tube, 2 a patient couch, 3 an object such as a patient, and 4 an X-ray detector array. The X-ray tube 1 and the X-ray detector array 4 are mounted to a gantry (not shown) so as to face each other with respect to the patient couch 2 interposed therebetween. The combination of the X-ray tube 1 and the X-ray detector array 4 is rotatable about a longitudinal axis of the patient 3. A data acquisition system 5 (referred to "DAS" hereinafter) collects transmission data derived from the X-ray detector array 4 which detects the X-ray dosage penetrated through the patient 3 as the result of the X-ray irradiation. An X-ray tube control section 6 supplies a high voltage to the X-ray tube 1 and drives the X-ray tube 1 under the control of a timing control section (to be discussed later) according to commands generated from a central control section (also to be discussed later). The X-ray tube control section 6 feeds back a signal indicating the irradiation of X-rays from the X-ray tube 1 to the timing control section. A mechanical control section 7 drives the gantry and also translates the patient couch 2 while keeping the gantry to the given position. In translating the patient couch 2, this section 7 counts the amount of movement of the patient couch 2 from its initial position thereof and outputs this counted value. A timing control section 8 is for controlling the operations of the various sections of the X-ray CT apparatus. A display/diagnostic control unit 10 is connected to the central control section 9.

The principle operation of the X-ray CT apparatus as described above will now be discussed.

The patient couch 2 carrying the patient 3 is assumed to be at the initial position. In the display/diagnostic control unit 10, the apparatus is set in the Scanographic scanning mode and a start command is generated. This start command is transferred through the timing control section 8 to the X-ray tube control section 6 and the mechanical control section 7. Then, the X-ray tube control section 6 supplies a high voltage to the X-ray tube 1 to start the pulsatory X-ray irradiation. In synchronism with this X-ray irradiation, the mechanical control section 7 starts its operation to translate the patient couch 2 at a given speed. At this time, the X-ray tube 1 and the X-ray detector array 4 are kept to the fixed position, different from the CT scanning mode. The X-rays transmitted through the patient 3 are detected by the X-ray detector array 4. The detected signal is properly processed by the DAS 5 under the control of the timing signal delivered from the timing control section 8. The finally processed digital signal of the DAS 5 is temporarily stored in the central control section 9. A similar Scanographic scanning operation proceeds during a predetermined period of time. At the termination of this period, the irradiation by the X-ray tube 1 of the one Scano scanning operation is completed. As a result, the data stored in the central control section 9 is sent to the display/diagnostic control unit 10 so as to display the Scanographic image on a monitor screen 20 (see FIG. 2). Then, desired tomographic scanning portions are specified by a track ball 10d (FIG. 3) of the display/diagnostic control unit 10 associated with the above-mentioned "horizontal lines" attendant with address Nos. 1 to 6 in FIG. 2. It is assumed that initially the horizontal line is displayed at the most uppermost part on the screen 20 and is gradually moved toward the lowermost lower part of the screen 20 by means of the track ball. If the desired first tomographic scanning portion is at the position as specified by the address number 1, the horizontal line is stopped here and a key-in button of the display/diagnostic control unit 10, which will be discussed later, is depressed. Then, a CT scanning command signal (to be discussed later), together with a position signal corresponding to the address number (it is assumed that this position signal is produced for every vertical deflection line of the screen 20), is sent to the central control section 9 and stored therein. The slice width of the tomograph is generally defined as 2 mm, 5 mm or 10 mm, and one of these is selected according to an allowable dosage of X-rays of the patient and a scanning condition of the affected part of the patient. The slice width employed here is of the type which, once selected, cannot be changed during the one Scano scanning operation.

Then, the "horizontal line" is moved by the track ball from address No. 1 to address No. 2 on the screen 20, and here a similiar key-in operation is repeated. In this case, a locus of the previous "horizontal line" is still left at the position of address No. 1 and is used as a reference by an operator. A similar key-in operation is further performed for the subsequent addresses Nos. 3 to 6. In this way, these designations on the tomographic scanning portions are completed.

It should be noted that the specified position on the screen 20, for example, by the address No. 3, must always correspond to the actual position of the patient 3. To this end, when the initial position of the patient couch 2 is set by the "horizontal line", an amount of movement of the patient couch 2 carrying the patient 3 as given by the mechanical control section 7 is also stored in the central control section 9 in accordance with the address number on the screen 20.

Then, a mode select button of the display/diagnostic control unit 10 is set to a CT scanning mode. Under this mode, the mechanical control section 7 starts to operate and the patient couch 2 returns to the initial position and stops there. When a CT scanning start button of the display/diagnostic control unit 10 is pushed, the patient couch 2 is moved to a position corresponding to address No. 1 and is stopped there. Thereafter the ordinary CT scanning operation is performed. Further, the subsequent CT scanning operations are effected in the CT scanning order under the automatic positioning of X-ray irradiation toward the patient. In this way, the one series of CT scanning operation is performed.

The detailed explanation to follow is an elaboration of the arrangement and operation of the central control section 9 and its related circuits such as the display/diagnostic control unit 10.

The display/diagnostic control unit 10 is composed of a cathode ray tube 10a and a console 10b. The cathode ray tube 10a displays both a Scanographic image and a CT image alternately. The console 10b is provided with the key board 10c, a track ball 10d and a mode select button 10e and so on. As described above, the "horizontal line" on the screen 20 is moved by the track ball 10d, and at a desired position of the tomographic scanning portion a scanning command signal is generated by the key-in operation on the keyboard 10c. The mode select button 10e is for selecting either the Scanographic scanning mode or the CT scanning mode. The button 10e also serves as a CT scanning start button.

Although not shown, a memory and a microprocessor for the position data of the Scanographic image on the screen 20 are provided in the display/diagnostic control unit 10, as mentioned above, and convert the specified CT scanning positions on the screen 20 into an actual positions of the patient 3, using the data from the image reconstruction portion 9b as a reference. The converted position information is added, as a actual position data signal, to the positioning command signal for the CT scanning. In other words, the combination of the memory and microprocessor functions as a position converting table.

An arrangement of the central control section 9 will be described. A CT image reconstruction portion 9a reconstructs a tomogram on the basis of the X-ray penetration data by a convolution technique, for example. The X-ray penetration data is collected by irradiating X-rays onto the patient 3, while the X-ray tube 1 and the detector array 4 are rotated about the patient couch 2. A Scanographic image reconstruction portion 9b is for reconstructing a Scano image on the basis of the penetrated data of X-rays. This penetrated data is obtained when the patient couch 2 is translated along the longitudinal axis thereof while the X-ray tube 1 and the X-ray detector array 4 (disposed opposite to the X-ray tube) are fixed to the gantry (not shown), and X-rays are irradiated into the patient 3 in synchronism with the translation of the patient couch 2. A main memory 9c stores a slice position specified by superimposing the "horizontal line" on a Scano image displayed on the screen 20 in the display/diagnostic control unit 10, and further stores a sequence of the CT scanning operations. An X-ray tube position memory portion 9d is for storing a present position of the X-ray tube 1 relative to the patient couch 2 in the form of the counted value produced from the mechanical control section 7. An operation portion 9e is for comparing a slice position read out from the main memory 9c (with a parameter of the amount of movement of the patient couch 2 from its initial position) with the present position of the X-ray tube 1 read out from the X-ray tube position memory portion 9d (with a parameter of the amount of movement of the patient couch 2 from its initial position), and calculates the amount of movement of the patient couch 2 so as to position the X-ray tube 1 directly above the slice position for taking a tomogram. A drive command portion 9f produces a drive command signal to the X-ray tube control section 6 and the mechanical control section 7 through the timing control section 8, in accordance with the amount of movement read out from the operation portion 9e and in the scanning order read out from the main memory 9c.

Figure 4:
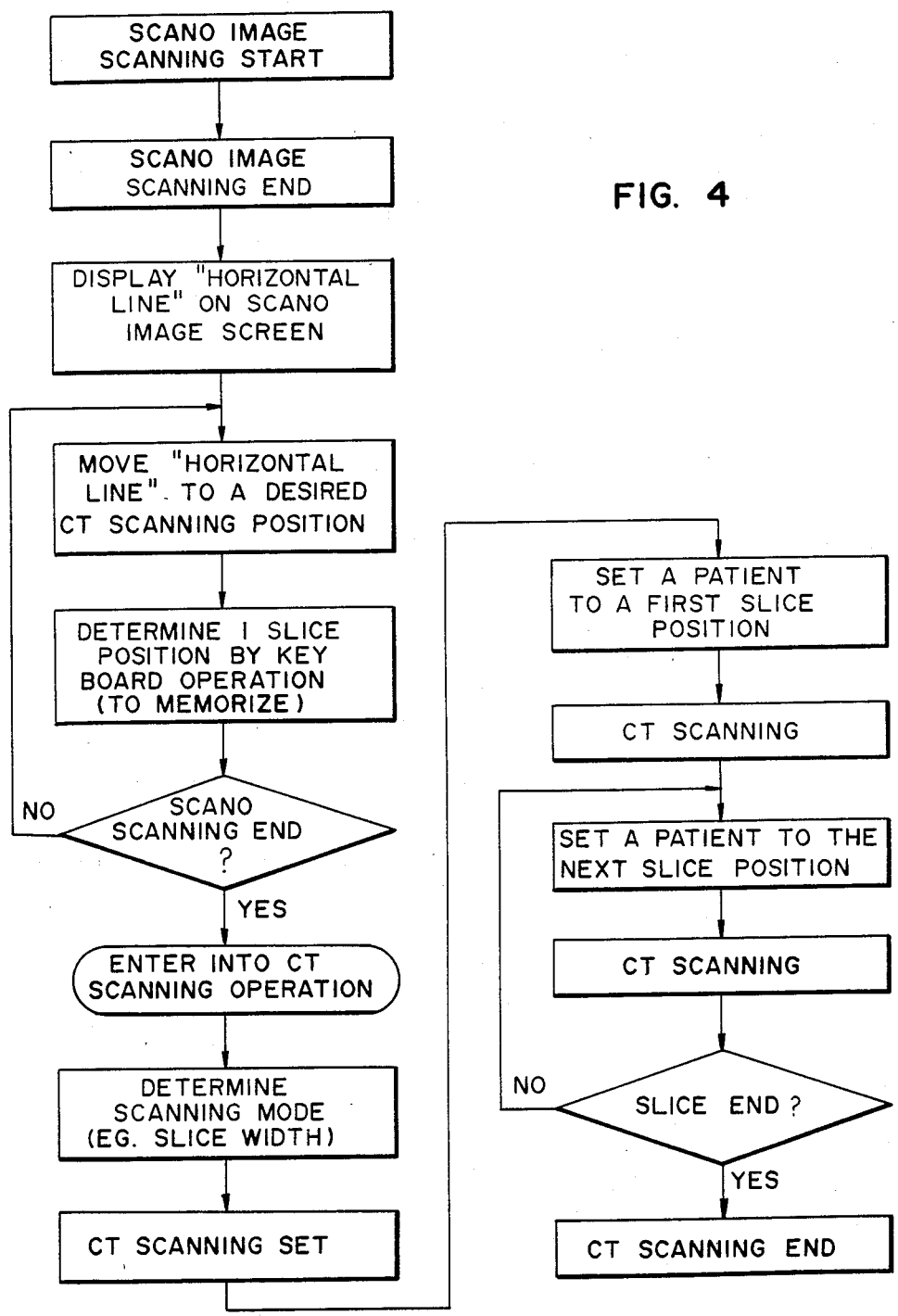

The operation of the above-mentioned arrangement will be described referring to FIG. 4 illustrating a flow chart of its operation. The Scanographic image scanning mode and subsequently the CT scanning mode will be given.

Figure 2:
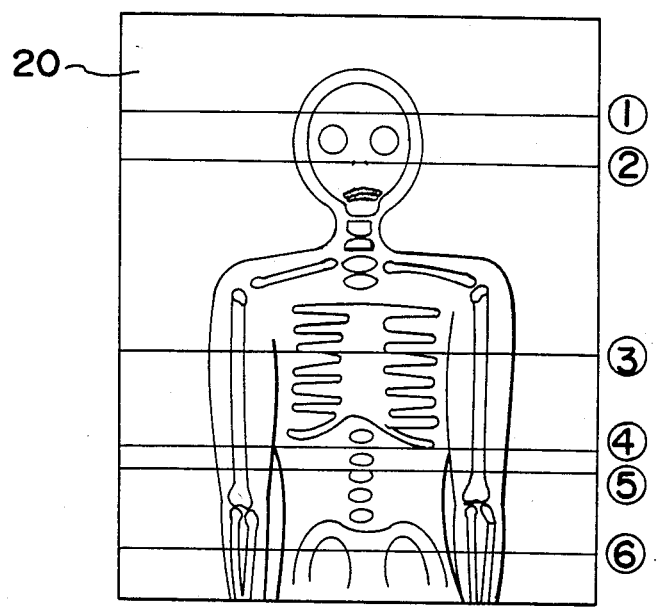
FIG. 2 shows schematically a screen of a cathode ray tube on which the Scano image is displayed together with the horizontal lines.
Figure 3:
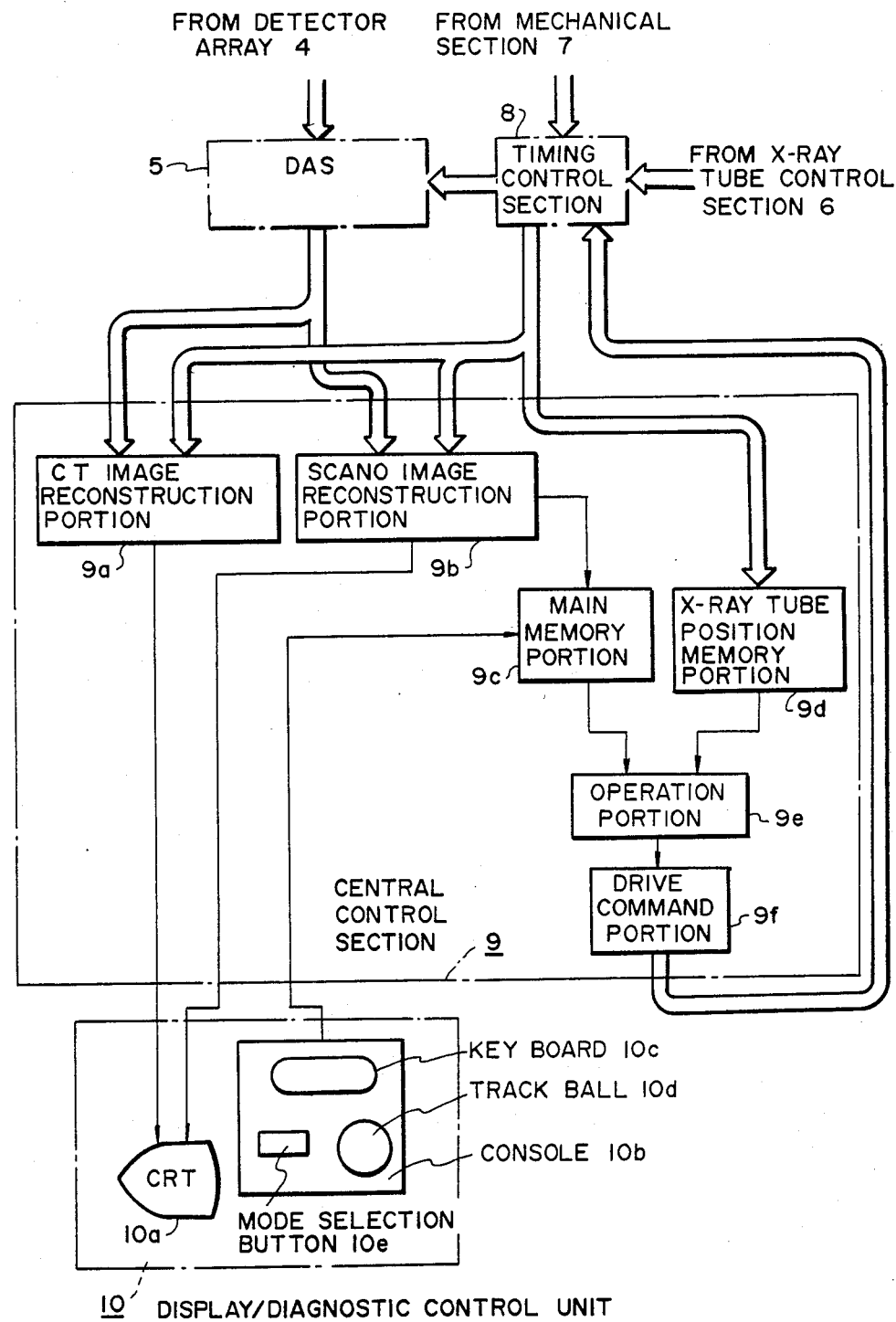
FIG. 3 shows a block diagram of a part of the preferred embodiment in greater detail and FIG. 4 is a flow chart of the Scano image scanning and the CT image scanning in accordance with the embodiment shown in FIG. 3.

First, the patient 3 laid on the patient couch 2 is set in front of a scanning hole of the gantry (not shown). Normally, the head of the patient 3 is positioned toward the scanning hole. Then, the patient couch 2 carrying the patient 3 is moved outward from its base. The couch 2 is inserted, for a given length, into the scanning hole, for example. At this time, the patient 3 and the X-ray tube 1 are set at the initial fixed (stationary) position and the mechanical control section 7 counts pulses from a pulse motor (not shown) for driving the patient couch 2. The counted value from the mechanical control section 7 is transferred through the timing control section 8 to the Scanographic image reconstruction portion 9b and the X-ray tube position memory portion 9d, both of which are arranged in the central control section 9. The X-ray tube control section 6 drives the X-ray tube 1 to cause it to irradiate X-rays at given slice intervals, in synchronism with the translation movement of the patient couch 2 driven by the mechanical control section 7. At the same time, it sends a signal representing the X-ray irradiation through the timing control section 8 to the Scanographic image reconstruction portion 9b in the central control section 9. The X-rays irradiated from the X-ray tube 1 and passing through the patient 3 are detected by the X-ray detector array 4 where they are converted into an electrical signal. The electrical signal is applied as digital penetration data to the DAS 5. The data collected by the DAS 5 are sent to the Scanographic image reconstruction portion 9b in the central control section 9. The Scanographic image reconstruction portion 9b reconstructs a Scano image on the basis of the penetrated data and applies it to the cathode ray tube 10a. The cathode ray tube 10a displays the Scano image of the patient 3, as shown in FIG. 2. The Scano image reconstruction portion 9b produces data signals on the slice width of the X-ray beam and the position of the X-ray tube 1 and applies them to the main memory 9c for storage. Such an arrangement is required because the desired position of the Scanographic image is always coincident with the position of the patient 3.

In the next step, the operator observes the Scanographic image on the cathode ray tube 10a to determine the CT scanning portions. Then, he operates the display/diagnostic control unit 10. In the operation, the "horizontal line" is moved to the position of the designated tomographic scanning portion on the Scano image in the scanning order, as desired, from addresses Nos. 1 to 6. That is, the "horizontal line" on the Scano image is moved to the position of address No. 1 by means of the track ball 10d and address number from the keyboard 10c is keyed in. This operation is subsequently repeated until address No. 6 has been keyed in. Finally, the display/diagnostic control unit 10 produces a imaging command signal representing the scanning position and scanning sequence of the "horizontal line" and applies them to the main memory 9c. A position of the X-ray tube 1, corresponding to the scanning width of the X-ray projection and the location of the "horizontal line", is read out from the table correspondingly containing the scanning width of the X-ray irradiation and the position of the X-ray tube 1 at that time. The positions of the X-ray tube 1 (referred to scanning positions) corresponding to the "horizontal lines" Nos. 1 to 6 are stored in the main memory 9c.

In the X-ray tube position memory 9d, the positions of the X-ray tube 1 produced from the mechanical control section 7 are successively rewritten in synchronism with the translation movement of the patient couch 2. Thus, the X-ray tube position memory 9d stores the position of the patient couch 2 as a present position when the patient couch 2 stops its movement. Upon completion of specifying the tomographic scanning portion, the operation portion 9e reads out the position of the X-ray tube 1, which corresponds to address No. 1 stored in the main memory 9c and the present position of the X-ray tube 1 stored in the X-ray tube position memory portion 9d. Then, it compares both the positions, and conveys the difference between the present position and the scanning position of the X-ray tube 1 to the drive command portion 9f. The drive command portion 9f signals an amount and a direction (forward and backward) of movement of the patient couch 2. After the patient couch 2 is moved a given distance, the drive command portion 9f also gives a scanning start command to the X-ray tube control section 6 and the mechanical control section 7. The X-rays irradiated from the X-ray tube 1, which is rotating about a longitudinal axis of the patient 3, are detected and are converted into electrical signals by the X-ray detector array 4. These electrical signals are collected by the DAS 5. The X-ray penetrated data produced from the DAS 5 are reconstructed for the original image formation by the main memory 9c and the keyboard 10c is operated to display a tomogram (first tomogram) of the tomographic scanning portion specified by address No. 1. Following this, the operation portion 9e reads out the position of the X-ray tube 1 corresponding to address No. 2 from the main memory 9c and the present position of the X-ray tube 1 from the Scanographic image reconstruction portion 9b (which has been rewritten to the position of the first tomogram). The second tomogram is displayed by the cathode ray tube 10a, as same as in the case of the first tomogram. Subsequently, the remaining third to sixth tomograms are displayed by the cathode ray tube 10a, through a similar process.

The advantages attained by the present invention will be given below. As described above, the tomographic scanning portions can be specified by freely setting the "horizontal line" at desired positions on the Scanographic image, of which intervals between the succeeding positions are different from each other. This feature solves the problem of the prior art which can provide a tomogram only at the tomographic scanning portion specified by a plurality of equidistant "horizontal lines" superimposed on the Scano image. Before a commencement of the CT scanning, all the tomographic scanning portions can be specified using a plurarity of the "horizontal lines" on the screen. This feature eliminates the need for specifying the tomographic scanning portion for every CT scanning. Further, the relative positions of the X-ray tube for the specified tomographic scanning portion and for the patient couch are stored and compared with each other, and then a tomogram of each tomographic scanning portion can automatically be taken in the order of the CT scannings. This feature improves an operability of the X-ray CT apparatus and reduces tomographing time.

While the present invention has been described using a specific embodiment, various changes and modifications may be made within the technical spirit and the scope of the invention.

In the above-mentioned embodiment, the CT scanning order was directed from top to bottom on the screen in successive order. This CT scanning order may be modified into a CT scanning order of the interlacing type in which, for example, a head portion is first specified, a bowel portion is then specified, and a head portion which is different from the previous head portion is specified.

It is evident that the present invention may be applied not only for the rotate/rotate type X-ray CT apparatus but also for a rotate/translate type or the rotate/stationary type X-ray CT apparatus. Also, in the above-mentioned embodiment, both the X-ray tube 1 and the detector array 4 were rotated with respect to the patient couch 2 during the CT scanning operation. It is obvious that only one of the X-ray tube 1 and detector array 4 is rotated with respect to the patient couch 2, and the remaining is kept stationary. Consequently either the X-ray tube 7 or the detector array 4 is moved relative to the patient couch 2 (the relative rotation). It is possible to employ two separate CRTs in the display/diagnostic control unit 10 for displaying the Scanographic image and the computerized tomographic image independantly on each screen.

Moreover it is possible to apply the principles of the invention to such a CT apparatus that both the automatic CT scanning operation and the automatic positioning of the X-ray irradiation toward the object (e.g. a patient) are realized.

What is claimed is:

1. An X-ray computerized tomographic apparatus for obtaining X-ray computerized tomographic images in cross-sectional planes of an object under examination at a plurality of designated positions along a longitudinal axis of the object, comprising:

source means for projecting fan-shaped radiation beams toward the object;

detector means for receiving said fan-shaped radiation beams that have penetrated through the object so as to produce output signals representative of intensities of the penetrated beams;

first control means for translating the object along the longitudinal axis of the object to obtain a scanogram of the object, in accordance with said fan-shaped radiation beams being projected toward the object from said source means and said detector means receiving said fan-shaped radiation beams penetrating through the object;

display means for displaying said scanogram and including means for selectively positioning a plurality of line markers for determining the plurality of designated positions thereon at which the tomographic images are to be taken and a plurality of successive numerals respectively corresponding to said line markers, said successive numerals indicating priority scanning orders of the tomographic images;

addressing means for automatically successively addressing the object in a sequence from the position of the line marker accompaning the smallest numeral until the position of the line marker accompanying the largest numeral; and second control means for effecting a rotation of said source and detector means about the object so as to acquire the tomographic images at the designed positions that have been addressed by the addressing means in the indicated priority order.

2. An X-ray computerized tomographic apparatus for obtaining X-ray computerized tomographic images in cross-sectional planes of an object under examination at a plurality of designated positions along a longitudinal axis of the object, comprising:

source means for projecting fan-shaped radiation beams toward the object;

detector means for receiving said fan-shaped radiation beams that have penetrated through the object so as to produce output signals representative of intensities of the penetrated beams;

first control means for translating the object along the longitudinal axis of the object to obtain a scanogram of the object, in accordance with said fan-shaped radiation beams being projected toward the object from said source means and said detector means receiving said fan-shaped radiation beams penetrating through the object;

display means for displaying said scanogram and including means for selectively positioning a plurality of line markers for determining the plurality of designated positions thereon at which the tomographic images are to be taken and a plurality of successive numerals respectively corresponding to said line markers, said successive numerals indicating priority scanning orders of the tomographic images;

addressing means for automatically successively addressing the object in a sequence from the position of the line marker accompanying the smallest numeral until the position of the line marker accompanying the largest numeral; and second control means for effecting a rotation of at least said source means about the object so as to acquire the tomographic images at the designated positions that have been addressed by the addressing means in the indicated priority order.

* * * * *